United States Patent [19]

LeBlanc et al.

[11] 4,136,037
[45] Jan. 23, 1979

[54] PHOSPHORAMIDE-HYDROXYMETHYL PHOSPHINE CONDENSATION PRODUCTS FOR TEXTILE FIRE RETARDATION

[76] Inventors: Destin A. LeBlanc, 115 Main St.; Robert B. LeBlanc, 99 Main St., both of Wickford, R.I. 02852

[21] Appl. No.: 872,970

[22] Filed: Jan. 27, 1978

Related U.S. Application Data

[63] Continuation of Ser. No. 643,574, Dec. 22, 1975, abandoned, which is a continuation-in-part of Ser. No. 552,501, Feb. 24, 1975, Pat. No. 4,020,262.

[51] Int. Cl.$^2$ ............................ C07F 9/22; C09K 3/28
[52] U.S. Cl. ................................. 252/8.1; 106/15 FP; 427/337; 427/341; 427/342; 427/381; 427/390 D; 428/276; 428/921; 260/551 P
[58] Field of Search ............... 260/551 P; 106/15 FP; 252/8.1; 427/337, 341; 428/276

[56] References Cited

U.S. PATENT DOCUMENTS

| 3,403,044 | 9/1968 | Chance et al. .................. 260/551 P |
| 3,681,060 | 8/1972 | Sello ..................................... 427/392 |

OTHER PUBLICATIONS

Date et al. CA 81 51051x (1974).
Date et al. CA 78 45003e (1973).

*Primary Examiner*—Winston A. Douglas
*Assistant Examiner*—J. V. Howard
*Attorney, Agent, or Firm*—Sprung, Felfe, Horn, Lynch & Kramer

[57] ABSTRACT

A water soluble product suitable for rendering textile materials flame retardant is produced by condensing (a) at least one hydroxymethyl phosphorus compound selected from the group consisting of $(CH_2OH)_4P-Y$ and $(CH_2OH)_3P$ with (b) about 0.33 to 3 times the molar amount of at least one substituted phosphoramide of the formula $PO(NR^1CH_3)(NR^2CH_3)(NR^3CH_3)$ wherein
$R^1$ and $R^2$ each independently is H or $CH_2OH$,
$R^3$ is H, $CH_2OH$, $CH_3$ or $[PO(NR^1CH_3)NCH_3]_{1-2}R^2$, and
Y is an equivalent amount of at least one anion of an acid, such as chloride, bromide, carbonate, nitrate, sulfate, phosphate or carboxylate.

Advantageously, the hydroxymethyl phosphorus compound is tetrakis(hydroxymethyl)phosphonium chloride or tris(hydroxymethyl)phosphine, and is present in about 1 to 3 times the phosphoramide wherein preferably $R^1$ and $R^2$ are hydrogen and $R^3$ is hydrogen or $PO(NHCH_3)_2$. The condensation product, preferably dissolved in water, is padded onto fabric, preferably a polyester/cotton blend, which is thereafter dried and cured thermally and/or chemically. When a thermal cure is used it is preferred to include an aminoplast in the treatment. The fabrics are flame retardent even after multiple launderings.

7 Claims, No Drawings

PHOSPHORAMIDE-HYDROXYMETHYL PHOSPHINE CONDENSATION PRODUCTS FOR TEXTILE FIRE RETARDATION

This is a continuation of application Ser. No. 643,574, filed Dec. 22, 1975, now abandoned, which is a continuation-in-part of application Ser. No. 552,501, filed Feb. 24, 1975, now U.S. Pat. No. 4,020,262, issued Apr. 26, 1977.

The present invention relates to preparing novel reaction products of hydroxymethyl phosphorus compounds and substituted phosphoric acid triamides and using such products for flameproofing textiles.

The compound tetrakis(hydroxymethyl)phosphonium chloride is well known to those skilled in the art as the basis for many flame-retardant finishes for cellulosic fabrics.

Phosphoramides such as tris(N',N'',N'''-methyl)phosphoramide have been used for flame-retarding cellulosic textiles according to U.S. Pat. No. 3,681,060.

U.S. Pat. No. 3,403,044 discloses the preparation of condensation products of tetrakis(hydroxymethyl)phosphonium chloride with either phosphoroxytriamide [P(O)(NH$_2$)$_3$] or dimethylamidophosphoroxydiamide [P(O)(NH$_2$)$_2$N(CH$_3$)$_2$] and the application of said products to cotton textiles using either a chemical cure or thermal cure.

It is well known to those trained in the art that the phosphine oxide structure is more effective in flame retarding polyester/cotton blends than are phosphorus flame retardants of higher oxidation states such as phosphoramides, phosphates, and phosphonates. On the other hand, those phosphorus compounds of higher oxidation states are more efficient on 100% cellulosic textiles.

It is an object of the present invention to provide compositions useful for flame retarding textile materials, especially polyester/cotton blends.

It is a further object to provide processes by which said compositions are used to flame retard textile materials.

These and other objects of the invention are realized in accordance with the present invention pursuant to which there is provided a water soluble condensation product of (a) at least one hydroxymethyl phosphorus compound selected from the group consisting of

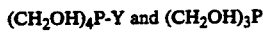

with (b) about 0.33 to 3 times the molar amount of at least one substituted phosphoramide of the formula

wherein

R$^1$ and R$^2$ each independently is H or CH$_2$OH,
R$^3$ is H, CH$_2$OH, CH$_3$ or [PO(NR$^1$CH$_3$)NCH$_3$]$_{1-2}$R$^2$, and
Y is an equivalent amount of at least one anion of an acid such as chloride, bromide, carbonate, nitrate, sulfate, phosphate, and carboxylate.

Illustrative of the hydroxymethyl phosphorus compounds are tetrakis(hydroxymethyl)phosphonium chloride, tetrakis(hydroxymethyl)phosphonium sulfate, tetrakis(hydroxymethyl)phosphonium acetate, tris(hydroxymethyl)phosphine, and the like. The preferred compounds are tetrakis(hydroxymethyl)phosphonium chloride and tris(hydroxymethyl)phosphine.

Illustrative of suitable phosphoramides are tris(N',N'',N'''-methyl)phosphoramide, tris(N',N'',N'''-hydroxymethyl-N',N'',N'''-methyl)phosphoramide, bis(N',N''-methyl)N''',N''''-dimethylphosphoramide, [(NHCH$_3$)$_2$PO]$_2$NCH$_3$ and [(NHCH$_3$)$_2$PONCH$_3$]$_2$PO NHCH$_3$. Preferred phosphoramides are those where R$^1$ and R$^2$ are methyl because of their ease of preparation.

The condensates of this invention contain the structures

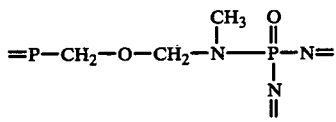

and/or 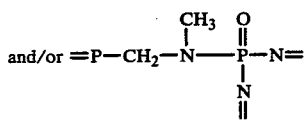

The condensation products of this invention are prepared by reaction of the hydroxymethyl phosphorus compound with the phosphoramide at temperatures of about 20°–120° C. preferably in the presence of a suitable solvent for both reactants. Preferably the solvent is water. The reaction may be exothermic and it may be necessary only to mix the two reactants together to form the products. It is preferable to insure sufficient reaction by heating the reaction mixture at temperatures of about 45°–90° C. for about 15 minutes to 4 hours, although any suitable times and temperatures may be used. The order of addition of the reactants to the reaction mixture sometimes affects the type and chain length of products formed. For example, in forming products with terminal P-CH$_2$OH groups, it is desirable to add the phosphoramide to the methylol phosphorus compound. For products with terminal P-NR$^1$CH$_3$ groups, the opposite order of addition is desirable. Alternatively, different but related products may be formed by adding the reactants simultaneously, either all at once or by gradual increments of each reactant. In any order of addition, it has also been found that preheating one or all of the reactants may be beneficial.

The ratio of the hydroxymethyl phosphorus compound to the phosphoramide may vary from about 0.33:1 to 3:1. Products of different mole ratios may have to be effectively applied by different means and the flame retardant properties imparted may vary. Fo example, products containing a multiplicity of P-CH$_2$OH groups, i.e., those made in ratios of about 1:1 to about 3:1, may be applied with either a chemical cure (with ammonia) or in a thermal cure involving coapplication with an aminoplast. Those products containing a multiplicity of P-NHCH$_3$ groups, i.e., those made in ratios of about 0.33:1 to about 1:1, can only be applied inefficiently by the ammonia cure technique. A thermal cure involving coapplication with an aminoplast is the most efficient way of fixing these products. Neither type of products provides any measure of durable flame retardance when merely padded onto the textile and dried and thermally cured. The mole ratio of methylol phosphorus compound to the phosphoramide is also significant in regard to the type of textile flame-retarded. For example, polyester/cotton blends require that at least part of the flame retardant chemical be active in the vapor phase. All-cotton textiles can be effectively flame retarded by chemicals that are effective in the vapor phase or by those effective in the condensed phase. The phosphorus from the phosphoramide is only effective in the condensed phase. The phosphorus from the hydroxymethyl phosphorus compound is effective in both the condensed and vapor phase. In treating polyester/cotton blends to meet such rigid standards as FF 3–71 (the Children's Sleepwear Standard), it has been found that generally at least half of the phosphorus applied must be in the form of the hydroxymethyl phosphorus compound. This is probably because of the necessity of having sufficient phosphorus that flame retards in the vapor phase.

The preferred hydroxymethyl phosphorus compounds are tetrakis(hydroxymethyl) phosphonium chloride and tris(hydroxymethyl)phosphine. The latter compound may be prepared by adding sodium hydroxide to a tetrakis(hydroxymethyl) phosphonium salt. The preferred phosphoramide is tris(N',N'',N'''-methyl) phosphoramide because of ease of preparation.

The materials or substrates to which this invention is applicable include textiles or webs formed of cotton, linen, regenerated cellulose, rayon, partially etherified and esterified cellulosic materials; textile blends of these fiber types with other fibers, such as polyester, nylon, acrylic, modacrylic, vinyon, wool, silk, etc.; other forms of cellulose such as wood and paper products; and proteinaceous textiles such as wool and silk. The textile materials may be in the form of fibers, yarns, fabics, (non-woven, woven, and knitted), webbings, and the like.

For textile applications it is generally desirable to treat textiles with condensation products of this invention such that about 1% to about 10%, preferably 3.5% to 6.5%, of phosphorus is applied to the textile.

For applications involving coapplication with an aminoplast and a thermal cure, any suitable aminoplast may be used, for example, trimethylol melamine, dimethylol melamine, dimethylol ethylene urea, dihydroxydimethylol ethylene urea, thiourea, mixtures thereof, and the like. About 2–50%, preferably about 10–40%, by weight of these aminoplasts is used based on the weight of the condensation products. It has generally been found with products of this invention that the handle of the fabric is most dependent on the amount and type of aminoplast resins used. It is desirable to apply a minimum amount of these resins consistent with good flame-retardance to obtain a soft handle. To obtain good flame-retardance and a good handle, it is generally preferable on a marginal treatment to increase the amount of phosphorus applied rather than to increase the amount of resin. On the other hand, if handle is not important, flame retardance may be improved by increasing the amount of resin applied. The preferred aminoplasts are combinations of urea and melamine, preferably polymethylolated, in about a weight ratio of 1:2 urea to melamine.

The pH of the treating bath may be adjusted to any desired level depending on the pH stabilities of the products in the bath. Normally the application of these products is made by padding the textile material with aqueous solutions of the condensation products and optionally the aminoplasts. However, other suitable means for impregnating the fabric may be used. The textile material is then dried or partially dried and then may be cured by: (1) a chemical cure in which the dried or partially dried fabric is exposed to ammonia--either gaseous or aqueous or a combination of the two; (2) a thermal cure in which the dried or partially dried fabric is subjected to elevated temperature for a time sufficient to fix the condensation products on and in the textile material, usually a temperature of about 120°–200° C. for about 10 minutes to 10 seconds.

The preferred cure for polyester/cotton blend fabrics is the thermal cure since this requires no special finishing equipment. For cotton textiles, it is preferable to use the chemical cure to avoid strength losses which may occur during a thermal cure of all-cotton fabrics. Unlike the ammonia cure application of tetrakis(hydroxymethyl)phosphonium chloride, better results are obtained with products of this invention by not adjusting the pH to about 7–8. Higher add ons are obtained at lower pH values of about 1 to 3.

The preferred method of treating textiles is to dissolve the condensation products, a methylol melamine resin, and urea in water with a wetting agent and softener. The textile material is padded with this aqueous solution, dried, and then cured. The textile material is thereafter washed in water containing a surfactant and an oxidizing agent such as sodium perborate or a combination of $H_2O_2$ and a base such as sodium silicate to remove unreacted material and improve the flame-retardance of the fabric.

If desired, the condensation product can be formed in the same vessel employed for treating the textile without isolation or separation of the condensate. Thus, the reactants are mixed, allowed to react, the concentration is adjusted to the desired value, suitable additives are supplied and the fabric immersed or padded in conventional manner. This permits the condensation to be carried out at textile finishing plants without the need for packaging the solution of condensation product.

The products and processes of the present invention differ from those in U.S. Pat. No. 3,403,044 in that one of the coreactants in U.S. Pat. No. 3,403,044 contains $P-NH_2$ bonds and is more prone to hydrolysis, especially in acid solutions such as water solutions of tetrakis(hydroxymethyl)phosphonium chloride. Thus the product may readily hydrolyze before reacting with the phosphonium compound and this hydrolysis is particularly detrimental to flame retardance in that it results in acidic P-OH groups which can pick-up calcium ions during launderings in hard water, calcium ions being known to deactivate phosphorus-based finishes. Phosphoryltriamide is also a water insoluble material (Handbook of Chemistry and Physics, 54th Edition, CRC Press, Cleveland, Ohio, p. B-117) which makes it difficult to react in water solutions. The phosphoramides used in the present invention are more resistant to hydrolysis, they are water soluble and thus readily react with the methylol phosphorus compounds.

The products disclosed in U.S. Pat. No. 3,403,044 are applied by a process of padding the product onto a cotton textile, drying the textile and curing using either a thermal cure or an ammonia cure, but without any aminoplast resin being used to fix these products. The thermal cure is efficient in fixing phosphorus (and therefore improving flame retardance) only for those products which gel soon after preparation. The products of the present invention do not gel at low ratios of the methylol phosphorus compound to the phosphoramide, as do products in U.S. Pat. No. 3,403,044. The products of the present invention are applied efficiently even with only a thermal cure when they are applied in conjunction with an aminoplast resin. During the thermal cure, the aminoplast resin may crosslink with itself, with the condensation products and with any reactive sites on the textile substrate to durably fix the condensation products to the textile substrate.

For an ammonia cure application, the products of the present invention offer the possibility of flame retarding cotton textiles at lower phosphorus levels. It is generally known that phosphoramides are more efficient than phosphines or phosphine oxides in flame retarding cotton fabrics (New Or Unusual Approaches to Flameproofing, A. W. Frank et al., 13th Cotton When a mixture of phosphoramide structures and phosphine oxide (or phosphine) structures is present on the fabric, lower levels of total phosphorus are possible as the fraction of phosphoramide structures increases. In comparing the reactions of tris-methyl phosphoramide and phosphoryl triamide with tetrakis(hydroxymethyl)phosphonium chloride, it is possible to prepare products containing terminal P-CH$_2$OH groups (which are capable of being chemically cured with ammonia) in mole ratios of phosphonium compound: phosphoramide approaching 1:1 for tris-methyl phosphoramide, but only approaching 2:1 for phosphoryl triamide. This is because the functionality of tris-methyl phosphoramide is 3, while the functionality of phosphoryl triamide is 6. Thus, products of this invention which can be effectively ammonia cured onto fabrics can be made containing 50% more phosphoramide phosphorus than similar products of U.S. Pat. No. 3,403,044. The products of this invention can thus flame-retard fabrics in an ammonia cure technique at much lower levels of phosphorus.

The following examples serve to illustrate the practice of the invention, but are not to be considered as limiting. In the examples tetrakis(hydroxymethyl)phosphonium chloride is abbreviated THPC and tris(N',N",N"'-methyl)phosphoramide is abbreviated TMPA. All parts are by weight unless otherwise specified.

EXAMPLE 1

A 2.5:1 molar THPC:TMPA condensation product was prepared by adding 152 parts of 80% aqueous THPC and 50 parts of 70% aqueous TMPA to a three-necked flask fitted with a thermometer, mechanical stirrer and water-cooled reflux condenser. Upon mixing, the temperature rose from 18° C. to about 40° C. The temperature of the reaction mixture was increased to 80° C. using external heating and was maintained at 80° C. for one hour. The reaction mixture was cooled to room temperature. Infrared spectra and thin layer chromatography confirmed formation of a condensation product. The resulting water soluble product contained 13.7% total phosphorus.

EXAMPLE 2

A 2.5:1 molar THPC:TMPA condensation product was prepared by adding 152 parts of 80% aqueous THPC to a flask fitted with a water-cooled reflux condenser, a thermometer, an addition funnel and a mechanical stirrer. The THPC was heated to 50° C. using a heating mantle. The heating mantle was removed and 50 parts of 70% aqueous TMPA were placed in the addition funnel and added to the THPC over a period of twenty minutes. During addition the temperature rose to 68° C.

The heating mantle was reapplied to maintain the temperature of the reaction at 65°–70° C. for one hour. The reaction mixture was cooled. The aqueous solution was analyzed by infrared spectrophotometry and by thin-layer chromatography to verify formation of a condensation product.

EXAMPLE 3

A 0.44:1 molar THPC:TMPA condensation product was prepared by adding 143 parts of 80% aqueous THPC, 265 parts of 70% aqueous TMPA, and 75 parts water to a flask fitted with a water-cooled reflux condenser, a thermometer and a mechanical stirrer. A heating mantle was used to heat the mixture to 60°–65° C. and to maintain it at that temperature range for one hour. The water solution of the condensate contained 12.6% total phosphorus.

EXAMPLE 4

Condensates were prepared in the mole ratios shown in Table I by adding the indicated parts of THPC and TMPA to a flask fitted with a water-cooled condenser, a thermometer and a mechanical stirrer. The temperature was raised to 60°–65° C. and maintained there for one hour using a heating mantle. The products were then cooled to room temperature and compared by thin layer chromatography using silica gel plates and a 65/35 chloroform/methanol mixture as eluant. The chromatogram was developed in iodine vapor. The TLC work indicated that, with decreasing mole ratios, material of higher molecular weight was formed.

Table

| Run | THPC:TMPA Mole Ratio | Parts 80% THPC | Parts 70% TMPA |
|---|---|---|---|
| A | 2.5:1 | 228 | 75 |
| B | 2.3:1 | 224 | 80 |
| C | 2.1:1 | 218 | 85 |
| D | 2.0:1 | 219 | 90 |
| E | 1.9:1 | 208 | 90 |
| F | 1.7:1 | 197 | 95 |
| G | 1.5:1 | 183 | 100 |
| H | 1.3:1 | 166 | 105 |

EXAMPLE 5

A 2.5:1 THPC:TMPA condensation product was prepared in a manner similar to that in Example 2 except that, upon completion of the addition of TMPA, heat was applied to bring the reaction to reflux (111°–112° C.) for one hour.

EXAMPLE 6

A 1.92:1 phosphonium phosphorus:TMPA condensate was prepared by adding 151 grams of Pyroset TKP (a commercial product of American Cyanamid Co. which is a 50/50 mole ratio mixture of tetrakis(hydroxymethyl)phosphonium acetate and tetrakis(hydroxymethyl)phosphonium phosphate containing 10% phosphonium phosphorus) and 50 grams of 70% aqueous TMPA to a flask fitted with a water-cooled condenser, a thermometer and a mechanical stirrer. A heating mantle was applied to raise the temperature to 60° C. and maintain it at that temperature for one hour. The reaction mixture was then cooled.

EXAMPLE 7

A 2.5:1 THPC:TMPA condensation product was prepared by adding 39.8 parts of 50% sodium hydroxide to a mixture of 152 grams of 80% aqueous THPC and 49 parts water. The caustic (0.8 moles based on the moles of THPC) was sufficient to raise the pH to 7.5 to produce an aqueous mixture of THPC and tris(hydroxymethyl)phosphine. The mixture was added to a flask fitted with a water cooled condenser, thermometer, mechanical stirrer and dropping funnel. Fifty parts of 70% aqueous TMPA were added to the dropping funnel and then were added dropwise to the reaction mixture over a period of 15 minutes. During addition, the reaction exothermed. The reaction temperature was kept at 50°–55° C. by use of an ice bath. Upon completion of the addition of the TMPA, a heating mantle was applied to keep the temperature at 50°–55° C. for an hour. The product was cooled to room temperature. It contained 9.5% phosphorus.

EXAMPLE 8

Tris(N',N'',N'''-methyl)N'-methylol phosphoramide $[P(O)(NHCH_3)_2N(CH_2OH)CH_3]$ was prepared by reacting paraformaldehyde (equivalent to one mole $CH_2O$) with one mole of TMPA in water at a pH of 10. A 2.5:1 THPC:tris(N',N'',N'''-methyl)N'-methylol phosphoramide condensation product was prepared by adding 152 parts of aqueous 80% THPC and 65 parts of a 65.5% aqueous solution of the methylolated phosphoramide to a flask fitted with a water-cooled condenser, a thermometer and a mechanical stirrer. External heat was applied to raise the temperature of the reaction to 80° C. and to maintain it there for one hour. The product was then cooled. It contained 12.7% phosphorus.

EXAMPLE 9

A treating bath was prepared by mixing 60 parts of the product from Example 1, 7 parts of Resloom HP (a product of Monsanto Co. which is substantially trimethylol melamine), 3.5 parts of urea, 0.1 part of Triton X-100 (a wetting agent from Rohm & Haas which is an alkyl, probably octyl, phenoxy polyethoxyethanol), and 29.4 parts of water. The treating bath was applied to a 3.4 oz./sq. yd. 50/50 polyester/cotton shirting fabric by padding to a 67% wet pick-up (WPU). The fabric was dried for five minutes at 104° C., cured for five minutes at 149° C., and then oxidized in a washing machine with water at 60° C. containing 0.1% of $H_2O_2$, 0.01% NaOH and 0.01% of $Na_2SiO_3$. The fabric had a dry add-on of 24.9%. It had a soft hand. It was laundered and tested according to FF 3-71 (the Children's Sleepwear Standard) with flame test results at intervals as follows:

| Launderings | Average Char Length (in.) |
| --- | --- |
| 0 | 4.0 |
| 10 | 3.8 |
| 25 | 4.0 |
| 50 | 3.7 |

EXAMPLE 10

A treating bath was prepared by mixing 59 parts of the product from Run A of Example 4, 7 parts of Resloom HP, 3.5 parts of urea, enough sodium hydroxide to raise the pH to 7, and water to a total of 100 parts. The treating bath was applied to a 3.4 oz./sq. yd 50/50 polyester/cotton shirting by padding to an 80% W.P.U. The fabric was dried at 104° C. for five minutes, cured at 149° C. for five minutes and oxidized as in Example 9. The fabric showed an initial char length of 3.9 inches and a char length of 3.2 inches after 50 launderings in the FF 3-71 test.

EXAMPLE 11

A treating bath was prepared by mixing 72 parts of the product from Example 6, 7 parts of Resloom HP, 3.5 parts of urea, 0.1 part of Triton X-100, and 12.4 parts of water. The bath was applied to a 3.4 oz./sq. yd. 50/50 polyester/cotton shirting at 67% W.P.U. The fabric was dried at 104° C. for five minutes, cured at 149° C. for five minutes, and oxidized as in Example 9. The fabric showed char lengths of 4.0 inches initially and 4.4 inches after 50 launderings by the FF 3-71 flame test.

EXAMPLE 12

Five treating baths were made by mixing the indicated amounts of condensation products with 6 parts of Resloom HP, 3 parts of urea, 0.1 part of Triton X-100 and water to a total of 100 parts:

Run I: 28.8 parts of the product from Run A of Example 4 and 27.7 parts of the product from Run B of Example 4, Run II: 26.6 parts of the product from Run C of Example 4, 17.1 parts of the product from Run D of Example 4 and 13.3 parts of the product from Run E of Example 4, Run III: 57.7 parts of the product from Run F of Example 4, Run IV: 55.1 parts of the product from Run G of Example 4, Run V: 16.3 parts of the product from Run G of Example 4 and 40.7 parts of the product from Run H of Example 4.

The baths were each padded onto a five oz./sq. yd. 50/50 polyester/cotton fabric (Style 9503 from Testfabrics, Inc.) at a 68–73% W.P.U. The fabric was dried at 99° C. for five minutes, cured at 149° C. for 3.5 minutes and oxidized as in Example 9. The add-ons and FF 3-71 flame test results after various laundering intervals are given below.

| | | Char Lengths (in.) at Laundering Intervals | |
| --- | --- | --- | --- |
| Run | % add-on | 0 | 25 |
| I | 23.3 | 2.7 | 2.3 |
| II | 22.5 | 2.5 | 2.5 |
| III | 21.2 | 2.9 | 1.8 |
| IV | 23.2 | 2.8 | 2.3 |
| V | 23.8 | 2.7 | 2.4 |

EXAMPLE 13

A treating bath was prepared by mixing 35 parts of the product from Example 3, 20 parts of Resloom HP, and 3 parts of Catalyst AC (an aqueous solution of 2-amino-2-methyl-1-propanol hydrochloride from Monsanto Co.). The treating bath was applied to a 3.5 oz./sq. yd. 50/50 polyester/cotton muslin fabric at an 86% W.P.U. The fabric was dried at 104° C. for five minutes, cured at 163° C. for five minutes, and oxidized as in Example 9. The fabric was tested by AATCC Test Method 34-1969 and showed a char length of 5.3 inches initially, 6.0 inches after 10 launderings, and 6.0 inches after 25 launderings.

EXAMPLE 14

A treating bath was prepared by mixing 42.5 parts of the product from Example 2, 0.1 part of Triton X-100, and 57.4 parts of water. The bath was padded onto a 3.3 oz./sq. yd. cotton flannelette at a 100% W.P.U. The fabric was dried at 99° C. to 10% moisture content. Eight times the molar amount of gaseous ammonia (based on phosphonium phosphorus) was passed through the fabric, and then the fabric was soaked in 5% aqueous ammonia for one minute. The fabric was then oxidized as in Example 9. The fabric was tested according to AATCC 34-1969 and showed char lengths of 4.2 inches initially, 5.0 inches after 5 launderings and 5.2 inches after 20 launderings.

EXAMPLE 15

A treating bath was prepared by mixing 57 parts of the product from Example 5, 7 parts of Resloom HP, 3.5 parts of urea, 0.1 part of Triton X-100 and 32.4 parts of water. The bath was aplied to a 5 oz./sq. yd. 50/50 polyester/cotton fabric at 71% W.P.U. The fabric was dried at 104° C. for five minutes, cured at 149° C. for 3.5 minutes and oxidized as in Example 9. The fabric showed FF 3-71 char lengths of 2.5 inches initially and 3.3 inches after 50 launderings.

EXAMPLE 16

A treating bath was prepared by mixing 47.2 parts of the product from Run A of Example 4, 6 parts of Resloom HP, 3 parts of urea, and 43.8 parts of water. The bath was padded onto a 4.3 oz./sq. yd. 56/35 polyester/cotton poplin at a 74% W.P.U. The fabric was dried at 104° C. for five minutes, cured at 149° C. for five minutes and oxidized as in Example 9. The fabric had char lengths of 2.1 inches initially and 2.7 inches after 25 launderings when tested by the FF 3-71 flame test.

EXAMPLE 17

A treating bath was prepared by mixing 47.4 parts of the product from Run A of Example 4, 8 parts of Aerotex M-3 (an 80% aqueous solution of a partially methylated methylol melamine from American Cyanamid Co.), 3 parts of urea, enough sodium hydroxide to raise the pH to 5 and water to a total of 100 parts. The bath was padded onto a 5 oz./sq. yd. 50/50 polyester/cotton fabric at 70% W.P.U. The fabric was dried for five minutes at 104° C., cured for five minutes at 149° C. and oxidized as in Example 9. The fabric had a char length of 2.7 inches after 10 launderings when tested by the FF 3-71 flame test.

EXAMPLE 18

A treating bath was prepared by mixing 47.4 parts of the product from Run A of Example 4, 12 parts of Resloom HP and 40.6 parts of water. The bath was padded onto a 3.4 oz./sq. yd. 50/50 polyester/cotton shirting at a 68% W.P.U. The fabric was dried at 104° C. for five minutes, cured at 149° C. for five minutes and oxidized as in Example 9. The fabric had a char length of 4.0 inches after 10 launderings when tested by the FF 3-71 flame test.

EXAMPLE 19

A treating bath was prepared by mixing 55 parts of the product from Run A of Example 4, 7 parts of urea and 38 parts of water. The bath was applied to a 3.4 oz./sq. yd. 50/50 polyester/cotton shirting fabric at a 74% W.P.U. The fabric was dried at 104° C. for five minutes, cured at 154° C. for four minutes and oxidized as in Example 9. The fabric showed char lengths of 5.5 inches initially and 5.5 inches after 15 launderings when tested by AATCC 34-1969.

EXAMPLE 20

A treating bath was prepared by mixing 62 parts of the condensation product prepared in Example 8, 7 parts of Resloom HP, 3.5 parts of urea and 27.5 parts of water. The bath was applied to a 5 oz./sq. yd. 50/50 polyester/cotton fabric at a 75% W.P.U. The fabric was dried for 5 minutes at 104° C., cured for 3.5 minutes at 149° C. and oxidized as in Example 9. The fabric had an add-on of 26%. It had char lengths of 2.0 inches initially and 3.5 inches after 50 launderings when tested by the FF 3-71 flame test.

EXAMPLE 21

A treating bath was prepared by mixing 83 parts of the product from Example 7, 7 parts of Resloom HP, 3.5 parts of urea, 0.1 parts of Triton X-100, and 6.4 parts of water. The bath was applied to a 3.4 oz./sq. yd. 50/50 polyester/cotton shirting fabric at a 79% W.P.U. The fabric was dried at 104° C. for five minutes, cured at 149° C. for 3.5 minutes and oxidized as in Example 9. The fabric had FF 3-71 char lengths of 2.8 inches initially and 4.1 inches after fifty launderings.

EXAMPLE 22

A 5 oz./sq. yd. 50/50 polyester/cotton blend fabric was padded with a 7% aqueous emulsion of tris(2,3-dibromopropyl)phosphate to a 75% W.P.U. The fabric was dried for five minutes at 104° C., cured for one minute at 210° C.) 0.01% aqueous soda ash and then dried. It was then padded to a 70% W.P.U. with a pad bath containing 50 parts of the product from Example 1, 5.8 parts Resloom HP, 2.9 parts urea, 0.1 part Triton X-100, and 41.2 parts water. The fabric was dried for five minutes at 104° C., cured for five minutes at 149° C. and then oxidized as in Example 9. The fabric had char lengths of 3.2 inches initially and 3.5 inches after fifty launderings when tested by FF 3-71.

EXAMPLE 23

(a) Preparation of Dimetric Phosphoramide

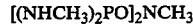

[(NHCH$_3$)$_2$PO]$_2$NCH$_3$

A round-bottomed flask was fitted with a gas inlet, an addition funnel, a stirrer and a condenser fitted with drying tube. 400 grams of chloroform were added as a solvent. Using a flow meter, monomethylamine was added under the surface of the chloroform at a rate of about 0.748 liter/minute. Simultaneously, POCl$_3$ was dropped in from the addition funnel at a rate of about 0.56 ml/minute. The reaction flask was cooled in an ice bath so that the temperature did not exceed 35° C. At the end of 7.2 minutes, the flow of both POCl$_3$ and methylamine were stopped.

The reaction product mixture was stripped of about 150 grams of chloroform to aid in the salting out of monomethylamine hydrochloride. 74.2 grams of salt were filtered out (93% recovery) and the chloroform solution stripped down under a vacuum to produce 53.8 grams of raw product.

The product was analyzed for phosphorus and chlorine and found to contain 13.3% methyamine hydrochloride and 86.7% of the dimeric phosphoramide. The product was dissolved in water to make a 60% aqueous solution of the dimeric phosphoramide.

(b) Preparation of Condensate

A 4:1 mole ratio of phosphonium salt: dimeric phosphoramide was prepared using 171.2 parts of 80% tetrakis (hydroxymethyl) phosphonium chloride and 72.2 parts of the 60% aqueous solution of the dimeric phosphoramide prepared in (a). The two components were mixed together as in Example 1, then heated at 65° C. for 45 minutes, and finally cooled to room temperature.

(c) Fabric Application

A pad bath was prepared containing:
55%: Condensate of (b)
7.4%: Resloom HP
3.7%: Urea
0.1%: Triton X-180
33.8%: Water It was applied by padding to a 3.4 oz./sq. yd. 50/50 polyester/cotton blend fabric at 80% wet pick-up. The fabric was dried at 104° C. for five minutes, cured at 149° C. for 3.5 minutes, and then oxidized as in Example 9. The fabric had a dry add-on of 29%. It had a char length of 4.5 inches after 50 launderings when tested according to FF 3-71.

EXAMPLE 24

A treating bath with a mole ratio of THPC:TMPA of 2.25:1 was prepared by first mixing 44 parts of 80% solution of THPC in water and 16 parts of a 70% solution of TMPA in water. The solution exothermed to 32° C. and was cooled to room temperature. To this solution were added 29.4 parts of water, 7 parts of Resloom HP, 3.5 parts of urea and 0.1 parts of Triton X-100 for a total of 100 parts of treating solution.

The treating bath was applied to a 3.4 oz./sq. yd. 50/50 polyester/cotton shirting fabric by padding to a 76% wet pick-up. The fabric was dried for five minutes at 104° C., cured for five minutes at 149° C. and then oxidized as in Example 9. The fabric had an average char length of 3.7 inches after 50 launderings in the FF 3-71 test.

It will be appreciated that the instant specification and examples are set forth by way of illustration and not limitation, and that various modifications and changes may be made without departing from the spirit and scope of the present invention.

What is claimed is:

1. A condensation product of (a) at least one hydroxymethyl phosphorus compound selected from the group consisting of
$(CH_2OH)_4P\text{-}Y$ and $(CH_2OH)_3P$
with (b) about 0.33 to 3 times the molar amount of at least one substituted phosphoramide of the formula $$PO(NR^1CH_3)(NR^2CH_3)(NR^3CH_3)$$

wherein
$R^1$ and $R^2$ each independently is H or $CH_2OH$,
$R^3$ is H, $CH_2OH$, $CH_3$ or $PO(NHCH_3)_2$
Y is an equivalent amount of at least one anion of an acid.

2. The condensation product of claim 1 in which $R^1$, $R^2$ and $R^3$ each is H.

3. The condensation product of claim 1 in which $R^3$ is $PO(NHCH_3)_2$ and $R^1$ and $R^2$ in all occurrences are hydrogen.

4. The condensation product of claim 1 in which the hydroxymethyl phosphorus compound is tetrakis (hydroxymethyl)phosphonium chloride.

5. The condensation product of claim 1 in which the hydroxymethyl phosphorus compound is present in about 1 to 3 times the molar amount of the phosphoramide.

6. An aqueous solution for rendering textile materials fire retardant containing about 15–60% by weight of the condensation product of claim 1.

7. The condensation product of claim 1 in which the hydroxymethyl phosphorus compound is tetrakis (hydroxymethyl)phosphonium sulfate.

* * * * *